US008218871B2

(12) United States Patent
Angell et al.

(10) Patent No.: US 8,218,871 B2
(45) Date of Patent: Jul. 10, 2012

(54) DETECTING BEHAVIORAL DEVIATIONS BY MEASURING RESPIRATORY PATTERNS IN COHORT GROUPS

(75) Inventors: Robert Lee Angell, Salt Lake City, UT (US); James R. Kraemer, Santa Fe, NM (US)

(73) Assignee: International Business Machines Corporation, Armonk, NY (US)

( * ) Notice: Subject to any disclaimer, the term of this patent is extended or adjusted under 35 U.S.C. 154(b) by 992 days.

(21) Appl. No.: 12/042,857

(22) Filed: Mar. 5, 2008

(65) Prior Publication Data

US 2009/0226043 A1    Sep. 10, 2009

(51) Int. Cl.
*G06K 9/00* (2006.01)
(52) U.S. Cl. ........ 382/181; 382/118; 382/124; 382/116; 382/115; 340/573.1; 340/573.2; 340/573.3
(58) Field of Classification Search .................. 382/181, 382/118, 124, 116, 115; 340/573.1, 573.2, 340/573.3
See application file for complete search history.

(56) References Cited

U.S. PATENT DOCUMENTS

| | | | | |
|---|---|---|---|---|
| 4,686,999 | A | * | 8/1987 | Snyder et al. .................. 600/529 |
| 5,928,156 | A | * | 7/1999 | Krumbiegel et al. ......... 600/529 |
| 6,535,131 | B1 | * | 3/2003 | Bar-Shalom et al. ...... 340/573.1 |
| 7,135,980 | B2 | | 11/2006 | Moore et al. |
| 2003/0133597 | A1 | * | 7/2003 | Moore et al. .................. 382/115 |
| 2009/0232357 | A1 | | 9/2009 | Angell et al. |

OTHER PUBLICATIONS

"IBM Digital Video Surveillance", IBM Corporation, Nov. 2006, pp. 1-4.
U.S. Appl. No. 12/049,818, filed Mar. 17, 2008, Angell et al.

* cited by examiner

*Primary Examiner* — Mike Rahmjoo
(74) *Attorney, Agent, or Firm* — Yee & Associates, P.C.; John R. Pivnichny

(57) ABSTRACT

A computer implemented method, apparatus, and computer usable program code for detecting behavioral deviations in members of a cohort group. In one embodiment, a member of a cohort group is identified. Each member of the cohort group shares a common characteristic. Respiratory metadata associated with the member of the cohort group is received in real-time as the respiratory metadata is generated. The respiratory metadata describes respiration associated with the member of the cohort group. Patterns of respiratory changes are identified using the respiratory metadata. The respiratory metadata is analyzed to identify the patterns of respiratory changes. In response to the patterns of respiratory changes indicating behavioral deviations in the member of the cohort group, the member of the cohort group is identified as a person of interest.

15 Claims, 8 Drawing Sheets

DETECTING BEHAVIORAL DEVIATIONS BY MEASURING RESPIRATORY PATTERNS IN COHORT GROUPS

BACKGROUND OF THE INVENTION

1. Field of the Invention

The present invention relates generally to an improved data processing system, and more specifically, to a computer implemented method and apparatus for video analysis. Still more particularly, the present invention is directed towards a computer implemented method, apparatus, and computer usable program product for detecting behavioral deviations by measuring respiratory patterns.

2. Background Description

Currently, more people are traveling over great distances by airplanes, trains, and buses for both work and pleasure. The increase in the number of passengers and customers in these facilities has lead to an increasing need for security. In an attempt to better monitor these environments, many businesses, transportation facilities, and public forums have installed cameras and other audio and/or video monitoring devices to record customers and/or passengers. A detective or security personnel may watch one or more monitors displaying closed circuit images recorded by these cameras to identify potential problem situations. However, these solutions require a human user to review the audio and video recordings.

BRIEF SUMMARY OF THE INVENTION

The illustrative embodiments provide a computer implemented method, apparatus, and computer usable program code for detecting behavioral deviations in members of a cohort group. In one embodiment, a member of a cohort group is identified. Each member of the cohort group shares a common characteristic. Respiratory metadata associated with the member of the cohort group is generated in real-time using respiratory data. The respiratory data describes respiration associated with the member of the cohort group. Patterns of respiratory changes are identified using the respiratory metadata. The respiratory metadata is analyzed to identify the patterns of respiratory changes. In response to the patterns of respiratory changes indicating behavioral deviations in the member of the cohort group, the member of the cohort group is identified as a person of interest.

DETAILED DESCRIPTION OF THE INVENTION

Figure 1:
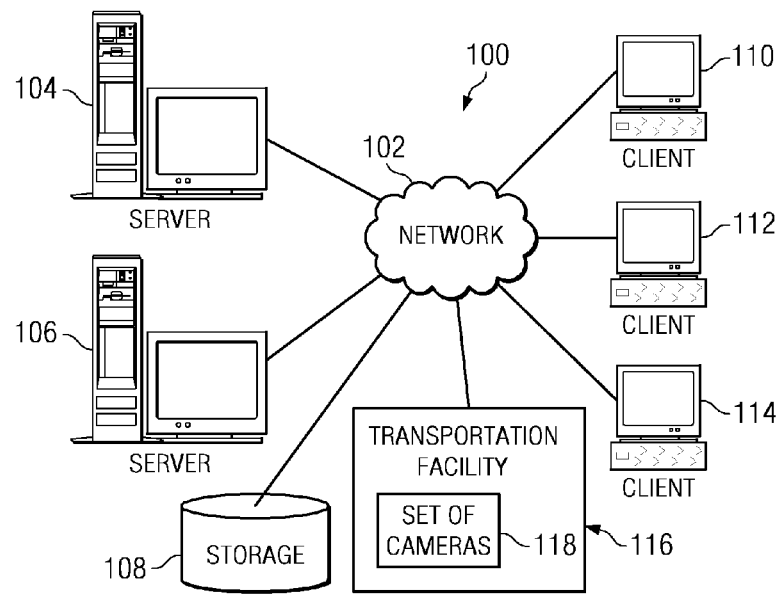
FIG. 1 is a network of data processing systems in which illustrative embodiments may be implemented.

As will be appreciated by one skilled in the art, the present invention may be embodied as a system, method or computer program product. Accordingly, the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present invention may take the form of a computer program product embodied in any tangible medium of expression having computer usable program code embodied in the medium.

Any combination of one or more computer-usable or computer-readable medium(s) may be utilized. The computer-usable or computer-readable medium may be, for example, but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disk read-only memory (CDROM), an optical storage device, a transmission media such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to wireless, wireline, optical fiber cable, RF, etc.

Computer program code for carrying out operations of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The present invention is described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions.

These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

Figure 2:
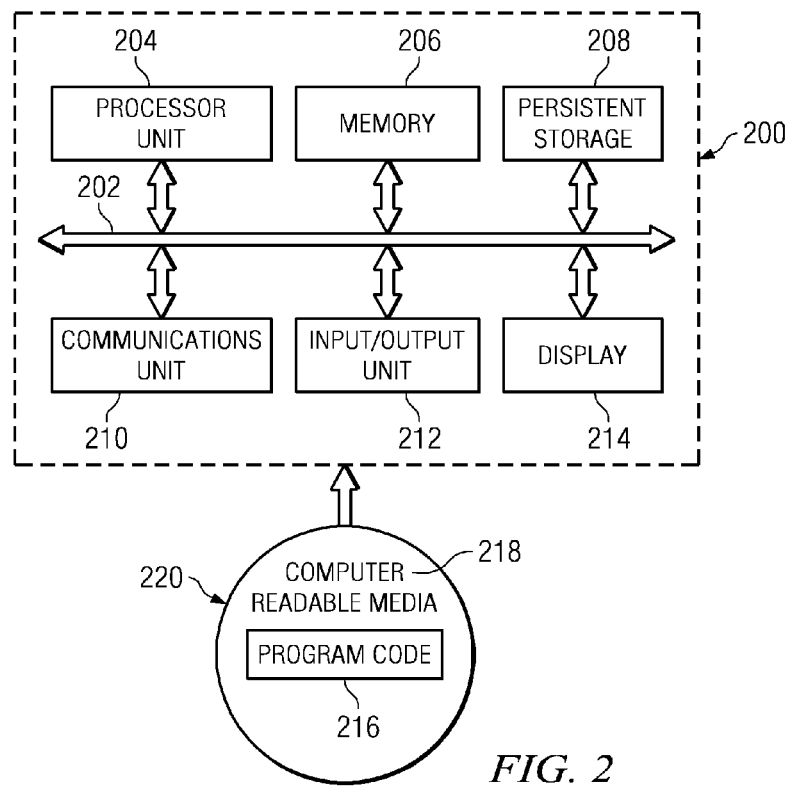
FIG. 2 is a block diagram of a data processing system in accordance with an illustrative embodiment of the present invention.

With reference now to the figures and in particular with reference to FIGS. 1-2, exemplary diagrams of data processing environments are provided in which illustrative embodiments may be implemented. It should be appreciated that FIGS. 1-2 are only exemplary and are not intended to assert or imply any limitation with regard to the environments in which different embodiments may be implemented. Many modifications to the depicted environments may be made.

FIG. 1 depicts a pictorial representation of a network of data processing systems in which illustrative embodiments may be implemented. Network data processing system 100 is a network of computers in which the illustrative embodiments may be implemented. Network data processing system 100 contains network 102, which is the medium used to provide communications links between various devices and computers connected together within network data processing system 100. Network 102 may include connections, such as wire, wireless communication links, or fiber optic cables.

In the depicted example, server 104 and server 106 connect to network 102 along with storage unit 108. In addition, clients 110, 112, and 114 connect to network 102. Clients 110, 112, and 114 may be, for example, personal computers or network computers. In the depicted example, server 104 provides data, such as boot files, operating system images, and applications to clients 110, 112, and 114. Clients 110, 112, and 114 are clients to server 104 in this example. Network data processing system 100 may include additional servers, clients, and other devices not shown.

Transportation facility 116 is a facility associated with transporting passengers from one point to another. Transportation facility 116 may include indoor facilities, as well as outdoor spaces, such as parking lots, sidewalks, airstrips, roadways, driveways, and/or any other indoor or outdoor facilities. For example, transportation facility 116 may be, without limitation, an airport, a bus depot, a train station, a dock, or any other type of transportation facility.

Set of cameras 118 may be implemented as any type of known or available device for capturing images and/or audio, such as, without limitation, digital video cameras, microphones, and/or infrared cameras. Set of cameras 118 may be located inside a building or structure associated with transportation facility, within a transportation vehicle, in an open air space associated with transportation facility, such as a sidewalk, roadway, or parking lot, or set of cameras 118 may include one or more cameras located inside a building or structure, one or more cameras located outside a building in an open air space, and/or one or more cameras inside a transportation vehicle, such as a train, bus, plane, or car.

In the depicted example, network data processing system 100 is the Internet with network 102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, network data processing system 100 also may be implemented as a number of different types of networks, such as for example, an intranet, a local area network (LAN), or a wide area network (WAN). FIG. 1 is intended as an example, and not as an architectural limitation for the different illustrative embodiments.

Turning now to FIG. 2, a diagram of a data processing system is depicted in accordance with an illustrative embodiment of the present invention. In this illustrative example, data processing system 200 includes communications fabric 202, which provides communications between processor unit 204, memory 206, persistent storage 208, communications unit 210, input/output (I/O) unit 212, and display 214.

Processor unit 204 serves to execute instructions for software that may be loaded into memory 206. Processor unit 204 may be a set of one or more processors or may be a multi-processor core, depending on the particular implementation. Further, processor unit 204 may be implemented using one or more heterogeneous processor systems in which a main processor is present with secondary processors on a single chip. As another illustrative example, processor unit 204 may be a symmetric multi-processor system containing multiple processors of the same type.

Memory 206, in these examples, may be, for example, a random access memory or any other suitable volatile or non-volatile storage device. Persistent storage 208 may take various forms depending on the particular implementation. For example, persistent storage 208 may contain one or more components or devices. In another example, persistent storage 208 may be a hard drive, a flash memory, a rewritable optical disk, a rewritable magnetic tape, or some combination of the above. The media used by persistent storage 208 also may be removable. For example, a removable hard drive may be used for persistent storage 208.

Communications unit 210, in these examples, provides for communications with other data processing systems or devices. In these examples, communications unit 210 is a network interface card. Communications unit 210 may provide communications through the use of either or both physical and wireless communications links.

Input/output unit 212 allows for input and output of data with other devices that may be connected to data processing system 200. For example, input/output unit 212 may provide a connection for user input through a keyboard and mouse. Further, input/output unit 212 may send output to a printer. Display 214 provides a mechanism to display information to a user.

Instructions for the operating system and applications or programs are located on persistent storage 208. These instructions may be loaded into memory 206 for execution by processor unit 204. The processes of the different embodiments may be performed by processor unit 204 using computer implemented instructions, which may be located in a memory, such as memory 206. These instructions are referred to as program code, computer usable program code, or computer readable program code that may be read and executed by a processor in processor unit 204. The program code in the different embodiments may be embodied on different physical or tangible computer readable media, such as memory 206 or persistent storage 208.

Program code 216 is located in a functional form on computer readable media 218 that is selectively removable and may be loaded onto or transferred to data processing system 200 for execution by processor unit 204. Program code 216 and computer readable media 218 form computer program product 220 in these examples. In one example, computer readable media 218 may be in a tangible form, such as, for example, an optical or magnetic disk that is inserted or placed into a drive or other device that is part of persistent storage 208 for transfer onto a storage device, such as a hard drive that is part of persistent storage 208. In a tangible form, computer readable media 218 also may take the form of a persistent storage, such as a hard drive, a thumb drive, or a flash memory that is connected to data processing system 200. The tangible form of computer readable media 218 is also referred to as computer recordable storage media. In some instances, computer readable media 218 may not be removable.

Alternatively, program code 216 may be transferred to data processing system 200 from computer readable media 218 through a communications link to communications unit 210 and/or through a connection to input/output unit 212. The communications link and/or the connection may be physical or wireless in the illustrative examples. The computer readable media also may take the form of non-tangible media, such as communications links or wireless transmissions containing the program code.

The different components illustrated for data processing system 200 are not meant to provide architectural limitations to the manner in which different embodiments may be implemented. The different illustrative embodiments may be implemented in a data processing system including components in addition to, or in place of, those illustrated for data processing system 200. Other components shown in FIG. 2 can be varied from the illustrative examples shown.

As one example, a storage device in data processing system 200 is any hardware apparatus that may store data. Memory 206, persistent storage 208 and computer readable media 218 are examples of storage devices in a tangible form.

In another example, a bus system may be used to implement communications fabric 202 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 206 or a cache such as found in an interface and memory controller hub that may be present in communications fabric 202.

The illustrative embodiments provide a computer implemented method, apparatus, and computer usable program code for detecting behavioral deviations in members of a cohort group. In one embodiment, a member of a cohort group is identified. Each member of the cohort group shares a common characteristic. Respiratory metadata associated with the member of the cohort group is received in real-time as the respiratory metadata is generated. The respiratory metadata describes respiration associated with the member of the cohort group. Patterns of respiratory changes are identified using the respiratory metadata. The respiratory metadata is analyzed to identify the patterns of respiratory changes. In response to the patterns of respiratory changes indicating behavioral deviations in the member of the cohort group, the member of the cohort group is identified as a person of interest.

In one embodiment, a continuous stream of video data associated with the member of the cohort group is received. The continuous stream of video data is received from a set of cameras. The continuous stream of video data is analyzed by a video analysis system to generate the respiratory metadata.

In another embodiment, infrared data associated with the member of the cohort group is received. The infrared data is received from a set of infrared sensors. The infrared data is analyzed by a video analysis system to generate the respiratory metadata. The respiratory metadata comprises metadata describing changes in infrared measurements of breath expired by the member of the cohort group.

In another embodiment, audio data associated with the member of the cohort group is received. The audio data is received from a set of audio sensors. The audio data is analyzed by video analysis system to generate the respiratory metadata. The respiratory metadata comprises metadata describing breath sounds and sounds associated with inspiration and expiration of air by a respiratory system of the member of the cohort group.

Figure 3:
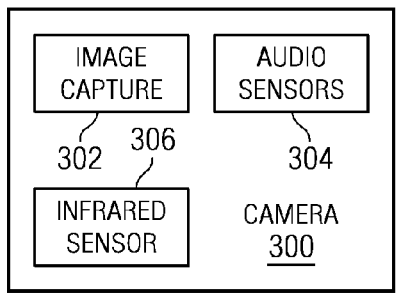
FIG. 3 is a block diagram of a camera for capturing data associated with a member of a cohort group in accordance with an illustrative embodiment.

FIG. 3 is a block diagram of a camera for capturing data associated with a member of a cohort group in accordance with an illustrative embodiment. Camera 300 is any type of known or available device for capturing images and/or audio, such as, without limitation, an optical image capture device, an infrared imaging device, a spectral or multispectral device, a sonic device, or any other type of image producing device. For example, camera 300 may include image capture 302.

Image capture 302 is a component for capturing video images, such as, without limitation, a digital video camera for taking moving video images, a digital camera capable of taking still pictures and/or a continuous video stream, a stereo camera, a web camera, and/or any other imaging device capable of capturing a view of whatever appears within the camera's range for remote monitoring, viewing, or recording of a person, object, or area. Image capture 302 may include various lenses, filters, and other optical devices such as zoom lenses, wide angle lenses, mirrors, prisms and the like to assist in capturing the desired view.

Audio sensors 304 comprise one or more devices for capturing sounds, such as, without limitation, a microphone. For example, audio sensors 304 may capture the sounds of a person's voice for a voice print analysis, the sounds of a person's breathing, the sounds of a person's footsteps as they walk, the sounds of a child crying, or any other sounds associated with a member of a cohort group.

Infrared sensor 306 is a thermographic camera, also referred to as a forward looking infrared, or an infrared camera, for generating images using infrared radiation. Infrared energy includes the radiation that is emitted by all objects as a function of the object's temperature. Typically, the higher the temperature emitted by an object, the more infrared radiation is emitted by the object. Infrared sensor 306 generates images showing the patterns of infrared radiation associated with heat emitted by people, animals, and/or objects. Infrared sensor 306 operates independently of the presence of visible light. Therefore, infrared sensor 306 can generate infrared images even in total darkness.

Camera 300 may be fixed in a particular orientation and configuration, or it may be programmable in orientation, light sensitivity level, focus or other parameters. For example, in one embodiment, camera 300 is capable of rotating, tilting, changing orientation, and panning. In another embodiment, camera 300 may be implemented as a robot camera or a mobile camera that is capable of moving and changing location, as well as tilting, panning, and changing orientation. Programming data may be provided via a computing device, such as server 104 in FIG. 1.

Camera 300 may also be located in a fixed location. However, even if camera 300 is located in a fixed position, camera 300 may still be capable of moving and/or rotating along one or more directions, such as up, down, left, right, and/or rotate about an axis of rotation to change a field of view of the camera without changing the fixed location of camera 300. Camera 300 may also be capable of rotating about an axis to keep a person, animal, vehicle or other object within the field of view of the camera, even if the person, animal, or object is in motion. In other words, the camera may be capable of moving about an axis of rotation in order to keep a moving object within the viewing range of the camera lens.

Camera 300 transmits the streaming video data, streaming audio data, and/or infrared images captured by camera 300 to a smart analysis engine. The smart analysis engine analyzes the video data, audio data, and/or infrared data and generated metadata describing the contents of the video data, audio data, and/or infrared images.

Figure 4:
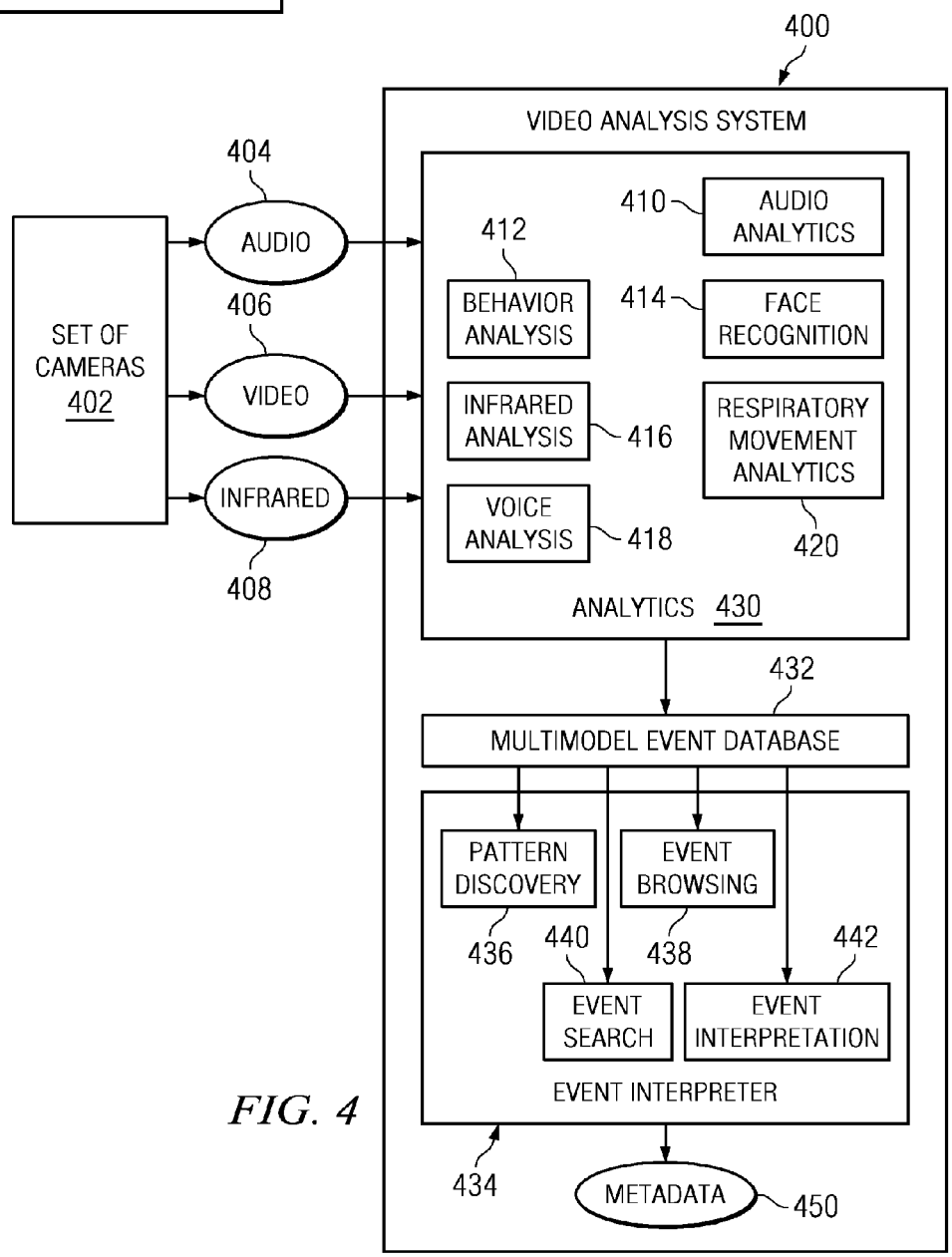
FIG. 4 is a block diagram of a video analysis system for generating respiration data associated with a member of a cohort group in accordance with an illustrative embodiment.

Turning now to FIG. 4, a block diagram of a video analysis system for generating respiration data associated with a member of a cohort group in accordance with an illustrative embodiment. Video analysis system 400 is software for analyzing the contents of information received from set of cameras 402 and generate metadata describing the contents of the information. The information may include a stream of audio data 404, a stream of video images 406, and/or infrared images 408.

Set of cameras 402 is a set of one or more cameras, such as camera 300 in FIG. 3. Each camera in set of cameras 402 may include an imaging device for generating images using visible light to generate video images 406, one or more microphones for capturing sounds to form audio data 404, and/or infrared camera technology to generate infrared images 408 using infrared radiation. Video images 406 and/or audio data 404 may include, without limitation, a sound file, a media file, a moving video file, a media file, a still picture, a set of still pictures, or any other form of image data and/or audio data.

Infrared images 408 includes one or more images showing thermal heat patterns associated with one or more persons, objects, and/or environments.

Video analysis system 400 is software architecture for generating metadata describing images and/or audio captured by set of video cameras 402. Video analysis system 400 may be implemented using any known or available software for audio analytics, image analytics, facial recognition, license plate recognition, and/or infrared analysis. In this example, video analysis system 400 may be implemented as, without limitation, IBM® smart surveillance system (S3) software.

Video analysis system 400 is software for dynamically processing audio data 404, video images 406, and/or infrared images 408 into respiratory metadata 409 in real time as audio data 404, video images 406, and/or infrared images 408 is received from set of cameras 402. Respiratory metadata 409 is metadata describing respiratory events captured in audio data 404, video images 406, and/or infrared images 408, such as body movements associated with respiration, such as expansion of the person's rib cage, breath sounds, and heat associated with exhaled breath.

Video analysis system 400 may optionally include software for processing audio data 404, video images 406, and/or infrared images 408 into event metadata describing other non-respiratory characteristics and events of a person. For example, video images 406 may include images of identifying features of the object, such as, without limitation, a face of a human user, a license plate or partial plate, an identification badge, a vehicle identification number (VIN), or any other identifying markings or features of the object. Video analysis system 400 may process video images 406 to identify the person and/or object using license plate recognition analytics, facial recognition analytics, behavior analysis analytics, or other analytics to identify a particular object and/or distinguish one object from another object. Likewise, audio data 404 may include sounds of a person's voice, sounds of a vehicle engine, and/or other sounds associated with a particular person, animal, and/or object. Video analysis system 400 may process the audio data 404 to identify a voice print identifying a person, a distinctive engine sound to identify a make, model, and/or year of a vehicle, or other distinctive sounds.

Video analysis system 400 utilizes computer audio and/or visual pattern recognition technologies, as well as audio and/or video analytics to analyze data captured by one or more situated cameras and microphones. The analysis of the video data generates events of interest in the environment. For example, an event of interest at a departure drop off area in an airport may include the position and location of cars, the position and location of passengers, and the position and location of other moving objects. In this embodiment, an event of interest includes, without limitation, body movements, sounds, and thermal energy associated with respiration by one or more people.

In this example, video analytics engine 400 architecture is adapted to satisfy two principles. 1) Openness: The system permits integration of both analysis and retrieval software made by third parties. In one embodiment, the system is designed using approved standards and commercial off-the-shelf (COTS) components. 2) Extensibility: The system should have internal structures and interfaces that will permit for the functionality of the system to be extended over a period of time.

The architecture enables the use of multiple independently developed event analysis technologies in a common framework. The events from all these technologies are cross indexed into a common repository or a multi-modal event database 432 allowing for correlation across multiple audio/video capture devices and event types.

Video analysis system 400 includes the following illustrative analytical technologies integrated into a single system to generate metadata describing one or more objects in an area of interest based on video data from set of cameras 402. The analytical technologies are technologies associated with audio analytics 410, behavior analysis 412, face recognition 414, infrared analysis 416, voice analysis 418, and/or respiratory movement analytics 420.

Audio analytics 410 comprises software analytics for identifying the source, type, strength, and patterns of sounds, such as a human voice, engine sounds, animal sounds, a baby cry, footsteps, ringing phones, or any other sounds. In this example, audio analytics 410 analyzes and identifies respiratory sounds.

Behavior analysis 412 is an analytics engine for identifying patterns of behavior, such as, without limitation, body movements associated with respiration, shallow breathing, and/or deep breathing. Behavior analysis 412 detects and tracks moving objects and classifies the objects into a number of predefined categories by analyzing metadata describing images captured by the cameras. As used herein, an object may be a human, an object, a container, a cart, a bicycle, a motorcycle, a car, or an animal, such as, without limitation, a dog. Behavior analysis 412 may be used to analyze images captured by cameras deployed at various locations, such as, without limitation, overlooking a roadway, a parking lot, a perimeter, or inside a facility. Behavior analysis 412 may also analyze the data generated by set of cameras 402 to identify other behaviors, such as walking speed, pacing, loitering, nervous gestures, such as, but not limited to, tapping of a foot or wringing of hands.

Video data 406 may include images of a person's face, an image of a part or portion of a car, an image of a license plate on a car, and/or one or more images showing a person's behavior. Face recognition 414 is software for analyzing images of a person's face and identifying features of the person's face for identification purposes. Infrared analysis 416 is a software analytics engine that analyzes infrared images 408 to identify the persons and/or objects associated with infrared radiation captured on infrared images 416. For example, and without limitation, infrared analysis 416 identifies patterns in infrared radiation in a series of infrared images 408 to identify thermal patterns associated with expired breath. The infrared patterns associated with the expired breath can then be processed to determine the frequency of breathing out, the rate of respiration, the depth of breathing, the shallowness of the breaths, and so forth.

Voice analysis 418 is a software analysis engine for analyzing audio data 404. Voice analysis 418 identifies human voices in audio data 404 and/or phonetics of human speech. Voice analysis 418 results may be used to compare a human voice print to known voice prints. If a match is found, the person associated with the human voice print may be identified.

Respiratory movement analytics 420 is a software analysis engine that analyzes video images 406 and/or infrared images 408 to identify movements of a person's chest, mouth, and/or nostrils associated with breathing. Respiratory movements analytics 420 identifies patterns in video images that correspond to a person's rib cage contracting and/or expanding with respiration, a person's abdomen expanding or relaxing as air is inhaled and/or exhaled, movements of a person's nostrils as air is inhaled and/or exhaled through the nose, and/or movements of a person's mouth as air is inhaled and/or exhaled through the mouth.

The analytics technologies in video analysis system 400 may also optionally comprise, without limitation, license plate recognition analytics, badge reader technology, and/or radar analytic technology (not shown). License plate recognition technology (not shown) may be utilized to analyze images captured by cameras deployed at the entrance to a facility, in a parking lot, on the side of a roadway or freeway, or at an intersection. License plate recognition technology catalogs a license plate of each vehicle moving within a range of two or more video cameras associated with video analysis system 400.

Facial recognition technology (not shown) is software for identifying a human based on an analysis of one or more images of the human's face. Facial recognition technology may be utilized to analyze images of objects captured by cameras deployed at entryways, or any other location, to capture and recognize faces.

Badge reader technology (not shown) may be employed to read badges. The information associated with an object obtained from the badges is used in addition to video data associated with the object to identify an object and/or a direction, velocity, and/or acceleration of the object. Events from access control technologies can also be integrated into video analysis system 400.

The data gathered from audio analytics 410, behavior analysis 412, face recognition 414, infrared analysis 416, voice analysis 418, and/or respiratory movement analytics 420, license plate recognition technology, facial recognition technology, badge reader technology, radar analytics technology, and/or any other analytics for analyzing video/audio data received from a camera or other video/audio capture device is received by video analysis system 400 for processing into events.

The events from all the above analysis technologies are cross indexed into a single repository, such as multi-modal database 432. In such a repository, a simple time range query across the modalities will extract license plate information, vehicle appearance information, badge information, object location information, object position information, vehicle make, model, year and/or color, and face appearance information. This permits an analysis server, such as analysis server 500 in FIG. 5, to easily correlate these attributes. The architecture of video analysis system 400 also includes one or more smart analytics engines, which house event analysis technologies, such as audio analytics 410, behavior analysis 412, face recognition 414, infrared analysis 416, voice analysis 418, and/or respiratory movement analytics 420, license plate recognition technology, facial recognition technology, badge reader technology, and/or radar analytics technology.

Video analysis system 400 further includes Middleware for Large Scale Analysis (analytics) 430, which provides infrastructure for indexing, retrieving, and managing event metadata. Each of the analytics technologies associated with analytics 430 can generate real-time alerts and generic event metadata. The metadata generated by the analytics technologies may be represented using, without limitation, extensible markup language (XML). In such a case, the XML documents include a set of fields which are common to all engines and others which are specific to the particular type of analysis being performed by one or more of the analytics technologies, such as, without limitation, audio analytics 410, behavior analysis 412, face recognition 414, infrared analysis 416, voice analysis 418, respiratory movement analytics 420, license plate recognition technology, facial recognition technology, badge reader technology, and/or radar analytics technology.

The metadata may be generated by analytics 430 via the use of, for example, web services data ingest application program interfaces (APIs) provided by analytics 430. The XML metadata is received by analytics 430 and indexed into predefined tables in multi-modal event database 432. This may be accomplished using, for example, and without limitation, the DB2™ XML extender, if an IBM® DB2™ database is employed. This permits for fast searching using primary keys. Analytics 430 provides a number of query and retrieval services based on the types of metadata available in the database.

Event interpreter 434 is software for interpreting and identifying patterns in events generated by the analytics technologies. Event interpreter 434 may include, for example, and without limitation, pattern discovery 436, event browsing 438, event search 440, and/or event interpretation 442. Each event has a reference to the original media resource, such as, without limitation, a link to the video file, a link to the infrared images, and/or a link to an audio file. This allows the user to view the images and/or listen to the sound file associated with a retrieved event.

Video analysis system 400 provides an open and extensible architecture for dynamic video analysis in real time without human intervention. Analytics engines, such as, without limitation, audio analytics 410, behavior analysis 412, face recognition 414, infrared analysis 416, voice analysis 418, respiratory movement analytics 420, license plate recognition technology, facial recognition technology, badge reader technology, and/or radar analytics technology preferably provide a plug and play framework for the video, infrared, and/or audio analytics. The event metadata generated by the analytics technologies is sent to multi-modal event database 432 in any type of programming language files, such as, without limitation, extensible markup language (XML) files. Web services API's in analytics 430 permit for easy integration and extensibility of the metadata. Various applications, such as, without limitation, event browsing, real time alerts, etc. may use structure query language (SQL) or similar query language through web services interfaces to access the event metadata from multi-modal event database 432.

Analytics 430 may be implemented as a C++ based framework for performing real-time event analysis. Analytics 430 is capable of supporting a variety of video/image analysis technologies and other types of sensor analysis technologies. Analytics 430 provides at least the following support functionalities for the core analysis components. The support functionalities are provided to programmers or users through a plurality of interfaces employed by analytics 430. These interfaces are illustratively described below.

In one example, standard plug-in interfaces may be provided. Any event analysis component which complies with the interfaces defined by analytics 430 can be plugged into analytics 430. The definitions include standard ways of passing data into the analysis components and standard ways of getting the results from the analysis components. Extensible metadata interfaces are provided. Analytics 430 provides metadata extensibility.

For example, consider a behavior analysis application which uses video capture and image analysis technology. Assume that the default metadata generated by this component is object trajectory and size. If the designer now wishes to add color of the object into the metadata, analytics 430 enables this by providing a way to extend the creation of the appropriate structures for transmission to the backend analytics 430. The structures may be, without limitation, extensible markup language (XML) structures or structures in any other programming language.

Analytics 430 provides standard ways of accessing event metadata in memory and standardized ways of generating and transmitting alerts to the backend Analytics 430. In many applications, users will need the use of multiple basic real-time alerts in a spatio-temporal sequence to compose an event that is relevant in the user's application context. Analytics 430 provides a simple mechanism for composing compound alerts via compound alert interfaces. In many applications, the real-time event metadata and alerts are used to actuate alarms, visualize positions of objects on an integrated display, and control cameras to get better surveillance data. Analytics 430 provides developers with an easy way to plug-in actuation modules which can be driven from both the basic event metadata and by user-defined alerts using real-time actuation interfaces.

Using database communication interfaces, analytics 430 also hides the complexity of transmitting information from the analytics technologies to multi-modal event database 432 by providing simple calls to initiate the transfer of information. The IBM analytics 430 may include a J2EE™ framework built around IBM's DB2™ and IBM WebSphere™ application server platforms. Analytics 430 supports the indexing and retrieval of spatio-temporal event metadata. Analytics 430 also provides analysis engines with the following support functionalities via standard web services interfaces, such as, without limitation, XML documents.

Analytics 430 provide metadata ingestion services. These are web services calls which allow an engine to ingest events into analytics 430 system. There are two categories of ingestion services: 1) Index Ingestion Services: This permits for the ingestion of metadata that is searchable through SQL like queries. The metadata ingested through this service is indexed into tables which permit content based searches, such as provided by analytics 430. 2) Event Ingestion Services: This permits for the ingestion of events detected in the analytics technologies, such as those provided by analytics 430. For example, a loitering alert that is detected can be transmitted to the backend along with several parameters of the alert. These events can also be retrieved by the user but only by the limited set of attributes provided by the event parameters.

Analytics 430 provide schema management services. Schema management services are web services which permit a developer to manage their own metadata schema. A developer can create a new schema or extend the base middleware for large scale analysis schema to accommodate the metadata produced by their analytical engine. In addition, system management services are provided by analytics 430.

The schema management services of analytics 430 provide the ability to add a new type of analytics to enhance situation awareness through cross correlation. For example, a model for a monitored transportation facility environment is dynamic and can change over time. There may be an increase in the number of travelers and/or different sounds present during holiday seasons than during non-holiday seasons. Thus, it is important to permit video analysis system 400 to add new types of analytics and cross correlate the existing analytics with the new analytics. To add/register a new type sensor and/or analytics to increase situation awareness, a developer can develop new analytics and plug them into analytics 430 and employ middleware for large scale analysis' schema management service to register new intelligent tags generated by the new smart analytics engine analytics. After the registration process, the data generated by the new analytics can become immediately available for cross correlating with existing index data.

System management services provide a number of facilities needed to manage video analysis system 400 including:

1) Camera Management Services: These services include the functions of adding or deleting a camera from the system, adding or deleting a map from the system, associating a camera with a specific location on a map, adding or deleting views associated with a camera, assigning a camera to a specific middleware system serve,r and a variety of other functionality needed to manage the system. 2) Engine Management Services: These services include functions for starting and stopping an engine associated with a camera, configuring an engine associated with a camera, setting alerts on an engine and other associated functionality. 3) User Management Services: These services include adding and deleting users to a system, associating selected cameras to a viewer, associating selected search and event viewing capacities to a user, and associating video viewing privilege to a user. 4) Content Based Search Services: These services permit a user to search through an event archive using a plurality of types of queries.

For the content based search services (4), the types of queries may include: A) Search by Time retrieves all events from event metadata that occurred during a specified time interval. B) Search by Object Presence retrieves the last 100 events from a live system. C) Search by Object Size retrieves events where the maximum object size matches the specified range. D) Search by Object Type retrieves all objects of a specified type. E) Search by Object Speed retrieves all objects moving within a specified velocity range. F) Search by Object Color retrieves all objects within a specified color range. G) Search by Object Location retrieves all objects within a specified bounding box in a camera view. H) Search by Activity Duration retrieves all events from respiratory metadata 409 with durations within the specified range. I) Composite Search combines one or more of the above capabilities. Other system management services may also be employed.

Figure 5:
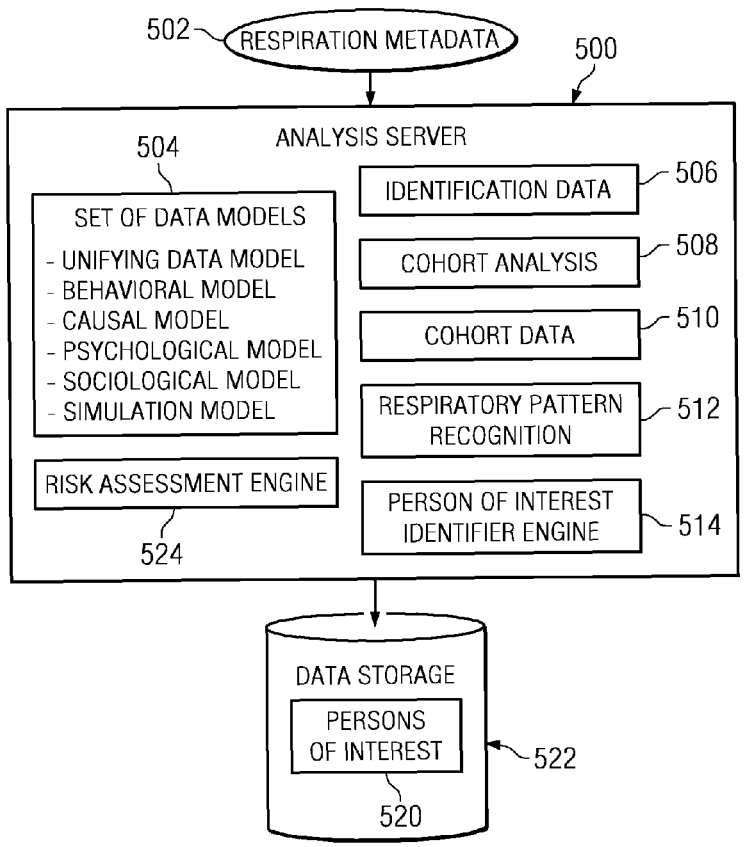
FIG. 5 is a block diagram of an analysis server for identifying a person of interest based on respiratory metadata in accordance with an illustrative embodiment.

FIG. 5 is a block diagram of an analysis server for identifying a person of interest based on respiratory metadata in accordance with an illustrative embodiment. Analysis server 500 may be a server, such as server 104 in FIG. 1 or data processing system 300 in FIG. 3. Analysis server 500 includes set of data models 504 for analyzing dynamic customer data elements and static customer data elements. Respiratory metadata 502 is metadata describing respiratory events associated with one or more persons. The one or more persons may be members of one or more cohort groups.

Set of data models 504 is one or more data models created apriori or pre-generated for use in analyzing respiratory metadata 502 to identify behavioral deviations associated with one or more persons. Set of data models 504 may include, without limitation, unifying data models, behavior models, causal models, psychological models, sociological models, and/or simulation models.

Identification data 506 is data describing one or more persons. In this example, identification data 506 includes point of contact data, profiled past data, current actions data, transactional history data, certain click-stream data, granular demographics, psychographic data, user provided registration data, account data and/or any other static customer data. Point of contact data is data regarding a method or device used by a user to interact with a data processing system associated with a transportation facility. The user interacts with the data processing system using a computing device or display terminal having a user interface for inputting data and/or receiving output. The device or terminal may be implemented as a display device provided by the transportation facility and/or a device belonging to the user.

If the display device is a display device associated with the transportation facility, details and information regarding the display device will be known to analysis server 500. However, if the display device is a display device belonging to the user, analysis server 500 may identify the type of display device using techniques such as interrogation commands, cookies, or any other known or equivalent technique.

An indication of a location for the point of contact may also be determined. For example, global positioning system (GPS) coordinates of the user may be determined if the user's computing device has such a capability whether by including a real time global positioning system receiver or by periodically storing global positioning system coordinates entered by some other method. Other location indications may also be determined such as post office address, street or crossroad coordinates, latitude-longitude coordinates or any other location indicating system.

Analysis server 500 may also determine the connectivity associated with the user's point of contact. For example, the user may be connected to a data processing system associated with the transportation facility in any of a number of ways such as a modem, digital modem, network, wireless network, Ethernet, intranet, or high speed lines including fiber optic lines. Each way of connection imposes constraints of speed, latency, and/or mobility which can then also be determined.

The profiled past comprises data that may be used, in whole or in part, for identifying the person, determining whether to monitor the person, and/or determining whether the person is a person of interest. Global profile data may be retrieved from a file, database, data warehouse, or any other data storage device. Multiple storage devices and software may also be used to store identification data 506. Some or all of the data may be retrieved from the point of contact device, as well. The profiled past may comprise an imposed profile, global profile, individual profile, and demographic profile. The profiles may be combined or layered to define the customer for specific promotions and marketing offers.

In the illustrative embodiments, a global profile includes data on the customer's interests, preferences, travel destinations, travel dates, and affiliations. Various firms provide data for purchase which is grouped or keyed to presenting a lifestyle or life stage view of customers by block or group or some other baseline parameter. The purchased data presents a view of one or more users based on aggregation of data points such as, but not limited to, geographic block, age of head of household, income level, number of children, education level, ethnicity, previous traveling accommodations, and purchasing patterns.

Current actions, also called a current and historical record, are also included in identification data 506. Current actions is data defining user behavior, such as listings of the travel related purchases made by the user, payments and refunds associated with the customer, and/or click-stream data from a point of contact device of the customer. Click-stream data is data regarding a user's navigation of an online web page of the merchant or supplier. Click-stream data may include page hits, sequence of hits, duration of page views, response to advertisements, transactions made, and conversion rates. Conversion rate is the number of times the customer takes action divided by the number of times an opportunity is presented.

In this example, profiled past data for a given customer is stored in analysis server 500. However, in accordance with the illustrative embodiments, profiled past data may also be stored in any local or remote data storage device, including, but not limited to, a device such as storage area network 108 in FIG. 1 or read only memory (ROM) 324 and/or compact disk read only memory (CD-ROM) 330 in FIG. 3.

Granular demographics are a source of static data elements that do not tend to change in real time, such as a person's name, date of birth, and address. Granular demographics provide detailed demographics information for one or more people. Granular demographics may include, without limitation, ethnicity, block group, lifestyle, life stage, income, and education data.

Cohort analysis 508 is a software component for generating one or more cohort groups based on attributes for people, animals, and/or objects. Cohort data 510 is data describing one or more cohort groups. A cohort group is a group of people, animals, and/or objects that share a common characteristic. For example, a cohort may include a group of plants. A different cohort may include people wearing baseball caps. A sub-cohort may include people wearing blue baseball caps.

Respiratory pattern recognition 512 is a software component for analyzing respiratory metadata 502 and identifying patterns in the respiratory metadata associated with one or more persons. If respiratory pattern recognition 512 identifies a respiratory pattern, respiratory pattern recognition 512 determines whether the respiratory pattern indicates normal behavior or behavioral deviations. For example, if the respiratory patterns indicate that a person's respiration is shallow and fast, the pattern of respiration may indicate behavioral deviations. Likewise, because travel is often stressful and exciting, if the respiratory patterns indicate a person's breathing is very controlled and unusually steady, the respiratory patterns may indicate a behavioral deviation.

Person of interest identifier engine 514 is software for identifying persons of interest. A person of interest is a person that is displaying unusual respiratory breathing patterns and/or other behavioral deviations. Person of interest identifier engine 514 stores an identifier associated with each person of interest in persons of interest 520 in data storage 522. Persons of interest 520 may be a file or any other data structure for storing identifiers identifying one or more persons of interest.

Risk assessment engine 524 is software for analyzing respiratory metadata 502 and/or other data associated with one or more persons to identify a risk associated with a person. Risk assessment engine 524 generates a risk level for each person of interest. Risk assessment engine 524 recommends one or more actions based on the level of risk associated with each person of interest. The actions may include searching, scanning, detaining, watching, following, or increasing monitoring of the person of interest. Likewise, risk assessment engine 524 may determine whether a person that is not identified as a person of interest should be monitored in the future. For example, if a person's breathing patterns do not indicate behavioral deviations, risk assessment engine 524 may consider other information and/or behavior associated with the person to determine whether the person should continue to be monitored or whether the person should be ignored and/or decrease the level of monitoring of the person.

Figure 6:
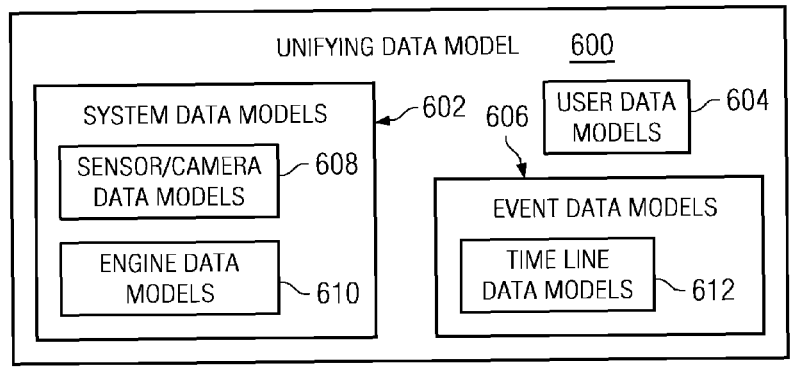
FIG. 6 is a block diagram of a unifying data model in accordance with an illustrative embodiment.

FIG. 6 is a block diagram of a unifying data model for processing respiratory event data in accordance with an illustrative embodiment. The respiratory event data is generated by a smart analysis system, such as smart analysis system 500 in FIG. 5. The respiratory event data may be processed by one or more data models in a set of data models, such as set of data models 504 in FIG. 5, to identify patterns in the respiratory events. A respiratory event is any event associated with respiration, such as, without limitation, an intake of breath, an expiration of breath, the rate of breathing, the length of time to inhale, length of time to exhale, the temperature of expired breath, and any other event associated with respiration.

Unifying data model 600 is an example of a data model for processing respiratory event data. In this example, unifying data model 600 has three types of data models, namely, 1) system data models 602 which captures the specification of a given monitoring system, including details like geographic location of the system, number of cameras, physical layout of the monitored space, and other details regarding the monitored environment; 2) user data models 604 models users, privileges and user functionality; and 3) event data models 606 which captures the events that occur in a specific sensor or zone in the monitored space. Each of these data models is described below.

System data models 602 have a number of components. These may include sensor/camera data models 608. The most fundamental component of sensor/camera data models 608 is a view. A view is defined as some particular placement and configuration, such as a location, orientation, and/or parameters, of a sensor. In the case of a camera, a view would include the values of the pan, tilt and zoom parameters, any lens and camera settings and position of the camera. A fixed camera can have multiple views. The view "Id" may be used as a primary key to distinguish between events being generated by different sensors. A single sensor can have multiple views. Sensors in the same geographical vicinity are grouped into clusters, which are further grouped under a root cluster. There is one root cluster per server.

Engine data models 610 utilize a wide range of event detection technologies, such as, without limitation, facial recognition, behavior analysis, and/or license plate recognition. User data models 604 captures the privileges of a given user. These may include selective access to camera views; selective access to camera/engine configuration and system management functionality; and selective access to search and query functions.

Event data models 606 represent the events that occur within a space that may be monitored by one or more cameras or other sensors. Time line data model 612 may also be employed as discussed above. Time line data models 612 uses time as a primary synchronization mechanism for events that occur in the real world, which is monitored through sensors. The event data model's basic schema allows multiple layers of annotations for a given time span.

Figure 7:
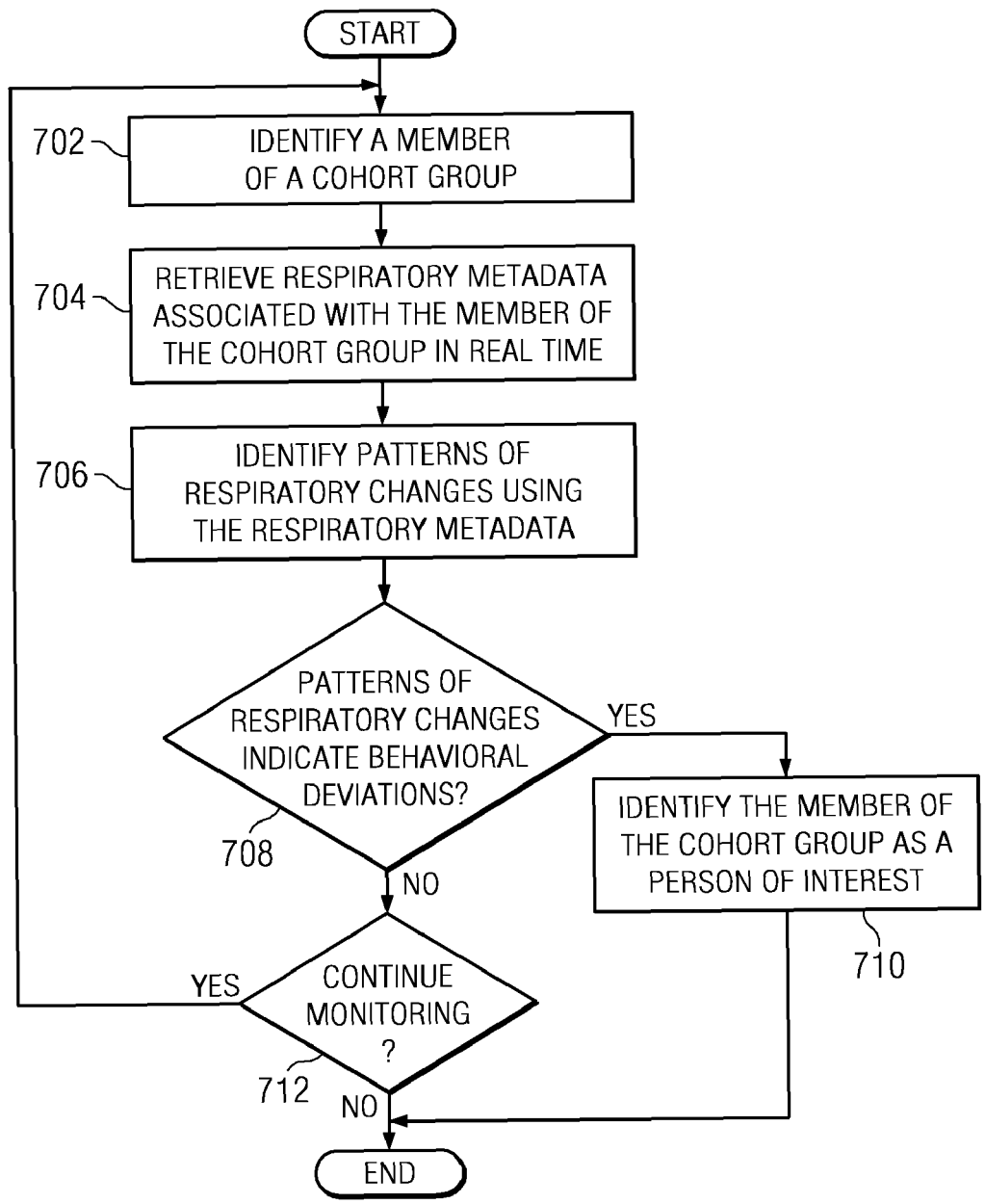
FIG. 7 is a flowchart illustrating a process for identifying a person of interest based on respiratory metadata in accordance with an illustrative embodiment.

FIG. 7 is a flowchart illustrating a process for identifying a person of interest based on respiratory metadata in accordance with an illustrative embodiment. Step 702 may be implemented by software for identifying cohorts, such as cohort analysis 508 in FIG. 5. Steps 704-706 may be implemented by software for identifying respiratory patterns in respiratory metadata, such as respiratory pattern recognition 512 in FIG. 5. Steps 708-712 are implemented by software for identifying persons of interest, such as person of interest identifier engine 514 in FIG. 5.

The process begins by identifying a member of a cohort group (step 702). Respiratory metadata associated with the member of the cohort group is retrieved in real time (step 704). The respiratory metadata may be retrieved from a data storage device or retrieved from software generating the respiratory metadata in real time from the video images, audio data, and/or infrared images as the video images, audio data, and/or infrared images are being gathered.

Patterns of respiratory changes are identified using the respiratory metadata (step 706). A determination is made as to whether patterns of respiratory changes indicate behavioral deviations (step 708). If the patterns of respiratory changes indicate behavioral deviations, the process identifies the member of the cohort group as a person of interest (step 710) with the process terminating thereafter. As a person of interest, one or more additional actions may be taken with respect to the person of interest. For example, the person of interest may be subjected to an increased level of monitoring, questioning by security personnel, a scanning by a metal detector or metal detector wand, checking by a drug sniffing dog, a pat down search, an x-ray, or other increased monitoring.

Returning to step 708, if the patterns of respiratory changes do not indicate behavioral deviations, a determination is made as to whether monitoring of the member of the cohort should continue (step 712). If monitoring should continue, the process returns to step 702. If monitoring should not continue, the process terminates thereafter.

Figure 8:
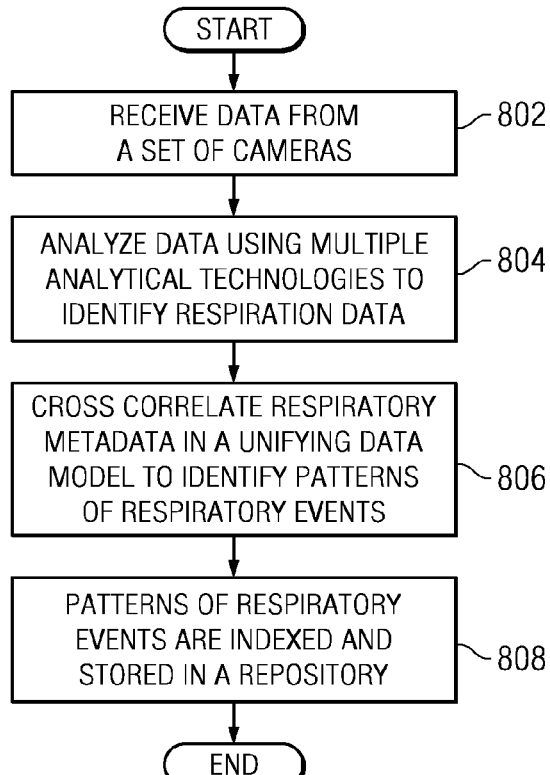
FIG. 8 is a flowchart illustrating a process for generating event data in accordance with an illustrative embodiment.

FIG. 8 is a flowchart illustrating a process for generating event data in accordance with an illustrative embodiment. The process in FIG. 8 may be implemented by software for generating respiratory metadata from a stream of video images, such as video analysis system 400 in FIG. 4.

The process begins by receiving data from a set of cameras (step 802). The set of cameras includes one or more cameras. The camera may be implemented as any type of camera, such as, without limitation, camera 300 in FIG. 3. The data includes, without limitation, streaming video images, streaming audio data, and/or infrared images.

The process analyzes the data using multiple analytical technologies to detect events to form respiratory metadata (step 804). The multiple technologies may include, for example, a behavior analysis engine, a license plate recognition engine, a face recognition engine, a badge reader engine, a radar analytic engine, respiratory movement analytics, audio analytics, voice analysis, and/or infrared analysis. The respiratory metadata is data describing respiratory events associated with a member of a cohort group. The respiratory metadata may describe, for example, movements of a person's chest or rib cage as the person breaths, breath sounds, wheezing breaths, rasping breaths, temperature of expired breath, frequency of expirations and/or inhalations, or any other respiratory events.

The respiratory metadata is cross correlated in a unifying data model to identify patterns of respiratory events (step 806). Cross correlating provides integrated situation awareness across the multiple analytical technologies. The cross correlating may include correlating respiratory events to a time line to associate events to define an integrated event. The patterns of respiratory events are indexed and stored in a repository, such as a database (step 808) with the process terminating thereafter.

In the example in FIG. 8, the database can be queried to determine whether an integrated event matches the query. This includes employing cross correlated information from a plurality of information technologies and/or sources. New analytical technologies also may be registered. The new analytical technologies can employ model and cross correlate with existing analytical technologies to provide a dynamically configurable surveillance system.

In this example, video data, audio data, and/or infrared data is received from a set of cameras. However, in other embodiments, the data may come from other sensor devices, such as, without limitation, a badge reader, a motion detector, a pressure sensor, or a radar.

Figure 9:
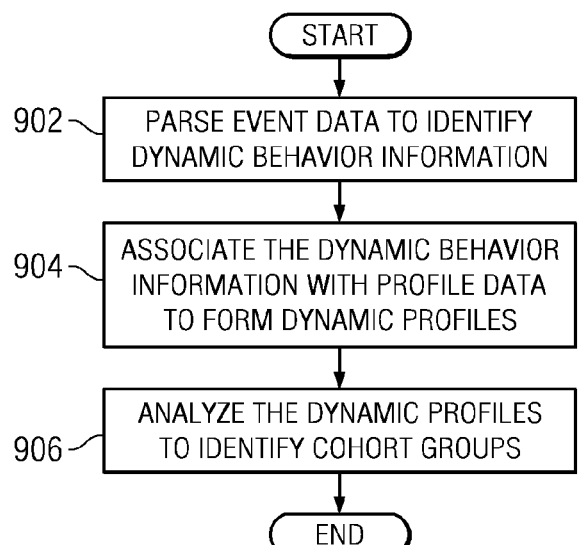
FIG. 9 is a flowchart illustrating a process for identifying members of a cohort group in accordance with an illustrative embodiment.

FIG. 9 is a flowchart illustrating a process for identifying members of a cohort group in accordance with an illustrative embodiment. The process in FIG. 9 is implemented by software for generating cohort groups, such as cohort analysis 508 in FIG. 5.

The process begins by parsing event data to identify dynamic behavior information (step 902). Dynamic behavior information is information describing behavior and/or events associated with people and/or objects that is generated substantially in real time as the behavior and/or events occur. The dynamic behavior information is associated with profile data to form dynamic data profiles (step 904) associated with the people and/or objects. The dynamic profiles are analyzed to identify cohort groups (step 906) with the process terminating thereafter. The cohort groups comprises the people and/or the objects.

Figure 10:
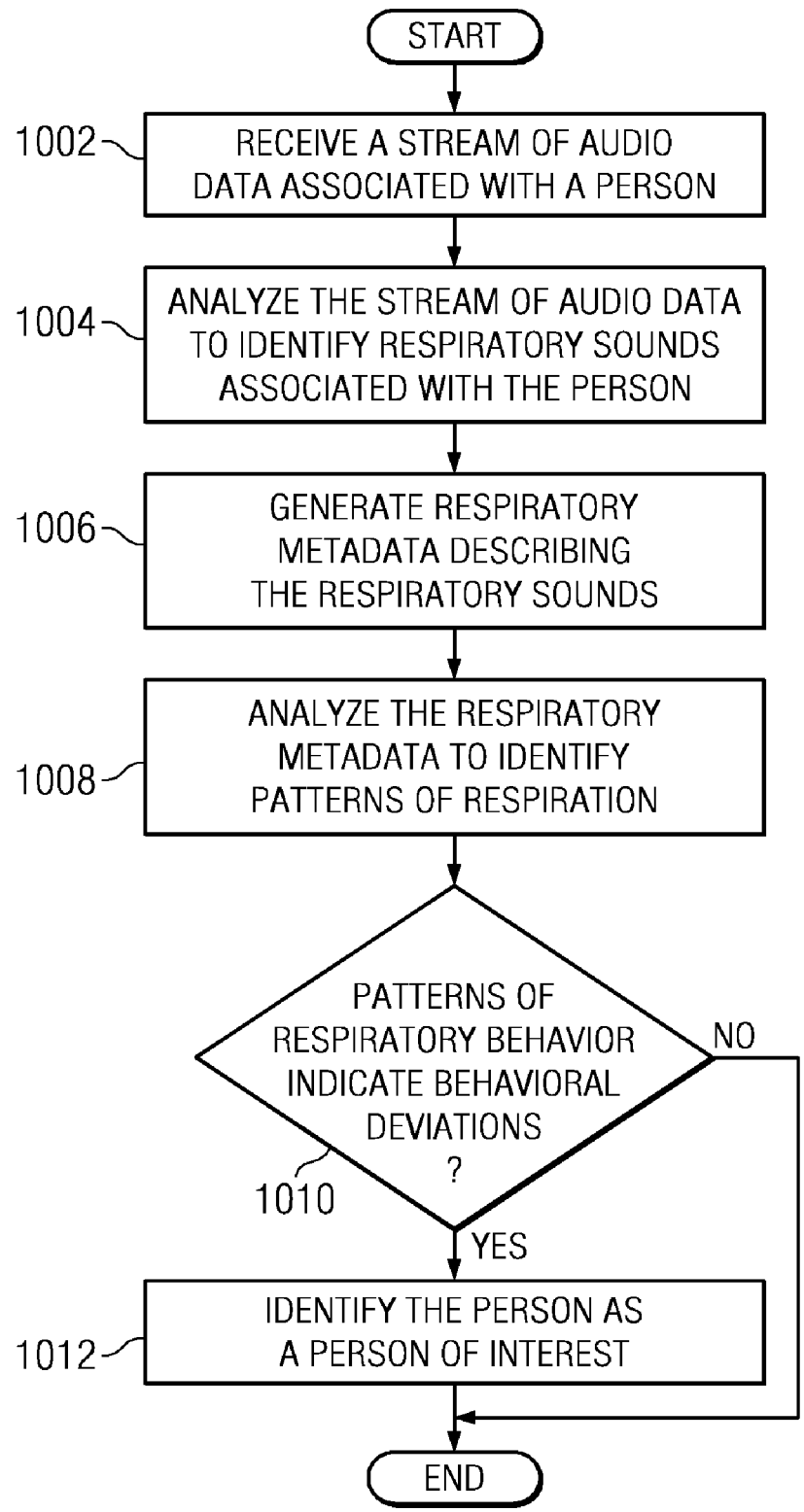
FIG. 10 is a flowchart illustrating a process for analyzing respiratory sounds associated with a member of a cohort group to identify a person of interest in accordance with an illustrative embodiment.

FIG. 10 is a flowchart illustrating a process for analyzing respiratory sounds associated with a member of a cohort group to identify a person of interest in accordance with an illustrative embodiment. The process in steps 1002-1006 in FIG. 10 may be implemented by software for generating respiratory metadata from audio data associated with a person, such as video analysis system 400 in FIG. 4. Steps 1008-1012 in FIG. 10 may be implemented by software for identifying behavioral deviations using respiratory metadata, such as analysis server 500 in FIG. 5.

The process begins by receiving a stream of audio data associated with a person (step 1002). The person may be a member of at least one cohort group. However, the person may also be a member of two or more different cohort groups. The stream of audio data is analyzed to identify respiratory sounds associated with the person (step 1004). Respiratory metadata is generated describing the respiratory sounds (step 1006).

The respiratory metadata is analyzed to identify patterns of respiration (step 1008). A determination is made as to whether patterns of respiration indicate behavioral deviations (step 1010). If the patterns of respiration do not indicate behavioral deviations, the process terminates thereafter. If the patterns of respiration indicate behavioral deviations, the person is identified as a person of interest (step 1012) with the process terminating thereafter.

Figure 11:
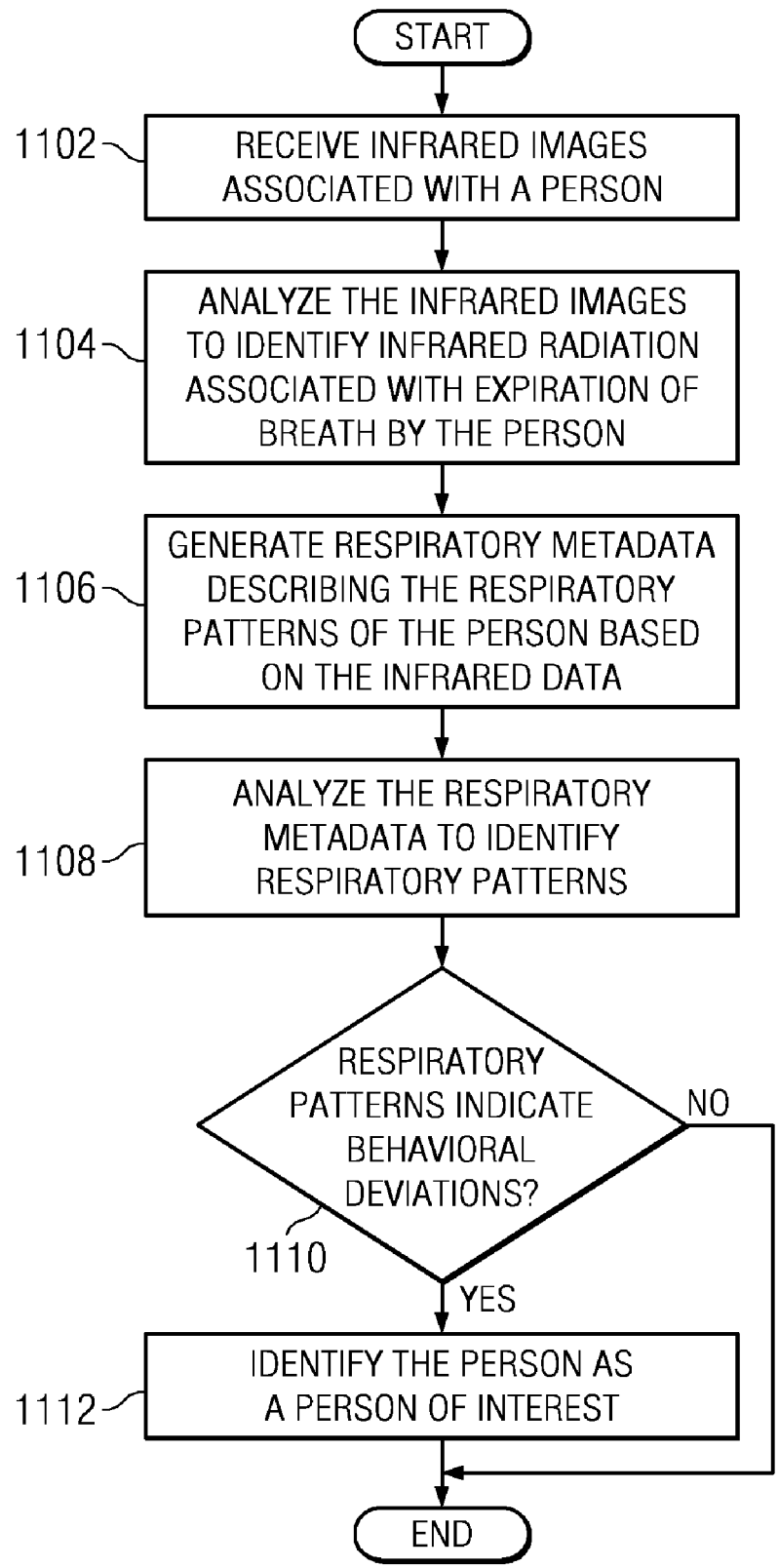
FIG. 11 is a flowchart illustrating a process for analyzing infrared data associated with respiration by a member of a cohort group to identify a person of interest in accordance with an illustrative embodiment.

Referring now to FIG. 11, a flowchart illustrating a process for analyzing infrared data associated with respiration by a member of a cohort group to identify a person of interest is depicted in accordance with an illustrative embodiment. The process in steps 1102-1106 may be implemented by software for generating respiratory metadata from infrared images associated with a person, such as video analysis system 400 in FIG. 4. Steps 1108-1112 in FIG. 11 may be implemented by software for identifying behavioral deviations using respiratory metadata, such as analysis server 500 in FIG. 5.

The process begins by receiving infrared images associated with a person from one or more infrared detectors (step 1102). The person may be a member of one or more cohort groups. The infrared images are analyzed to identify infrared radiation associated with expiration of breath by the person (step 1104). In other words, the infrared images shows the heat associated with breath expired from a person's body. Respiratory metadata describing the respiratory patterns of the person is generated using the infrared data to form respiratory metadata (step 1106).

The respiratory metadata is analyzed to identify respiratory patterns (steps 1108). A determination is made as to whether the respiratory patterns indicate behavioral deviations (step 1110). If the patterns of respiration do not indicate behavior deviations, such as abnormally fast breathing, abnormally shallow breathing, excessively controlled breathing, erratic breathing, a person holding their breath, or other abnormalities, the process terminates thereafter. Returning to step 1110, if the respiratory patterns do indicate behavioral deviations, the person is identified as a person of interest (step 1112) with the process terminating thereafter.

Figure 12:
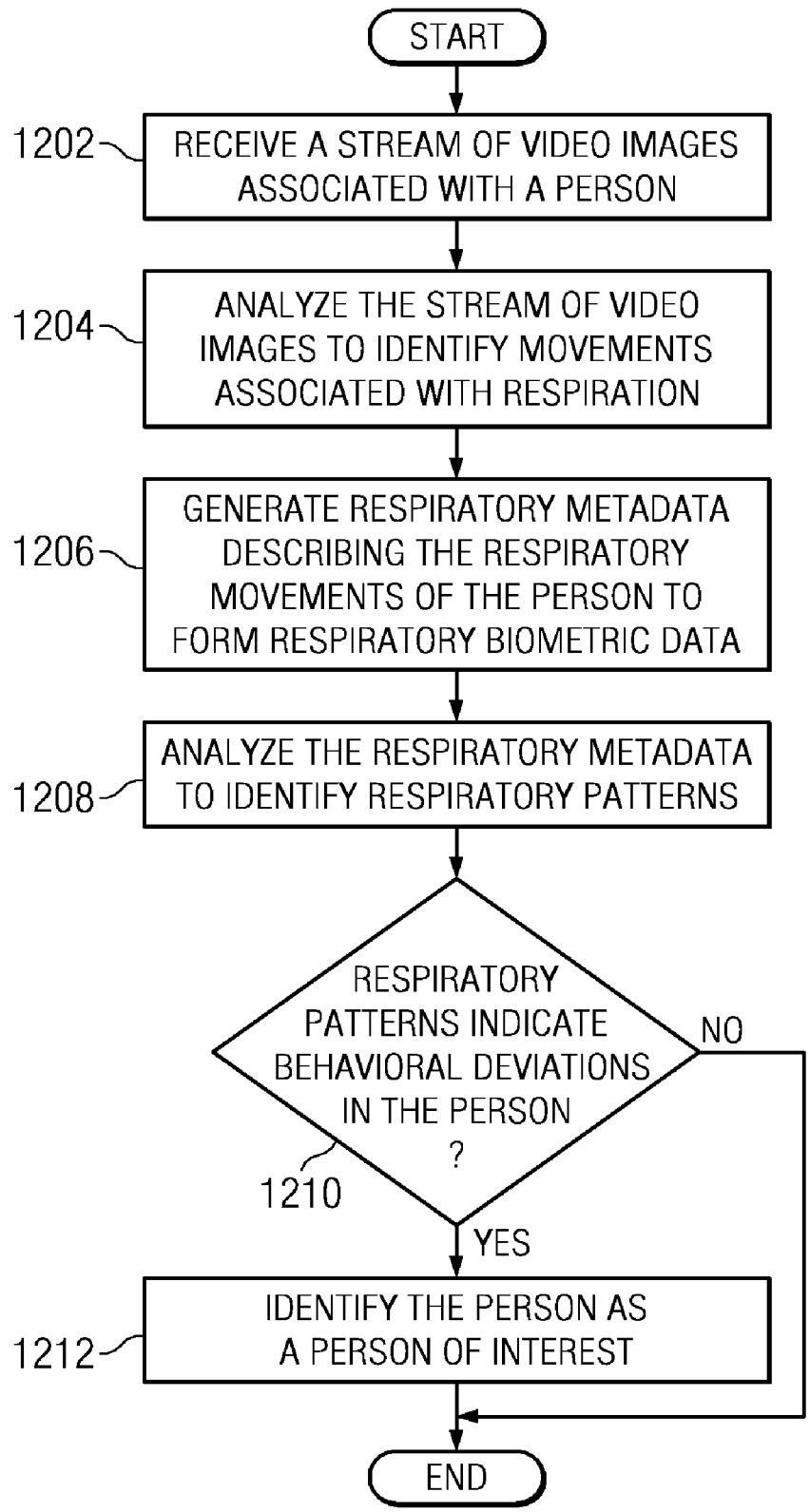
FIG. 12 is a flowchart illustrating a process for analyzing video data associated with respiratory movements by a member of a cohort group to identify a person of interest in accordance with an illustrative embodiment.

FIG. 12 is a flowchart illustrating a process for analyzing video data associated with respiratory movements by a member of a cohort group to identify a person of interest in accordance with an illustrative embodiment. The process in steps 1202-1206 in FIG. 12 is implemented software for generating respiratory metadata from a stream of video images of the one or more humans, such as video analysis system 400 in FIG. 4. Steps 1208-1212 in FIG. 12 may be implemented by software for analyzing respiratory metadata to detect behavioral deviations, such as analysis server 500 in FIG. 5.

The process begins by receiving a stream of video images associated with a person (step 1202). The person may be a member of one or more cohort groups. The steam of video images includes images of the person. The stream of video images is analyzed to identify movements associated with respiration (step 1204). The movements associated with respiration may include physical movements as the person's chest rises and falls during respiration, movements as the person's abdomen and/or rib cage expands outward and contracts inward during respiration, movements of clothing, facial hair, veils, or other objects as the person inhales and exhales, and/or any other movements of objects corresponding to respiratory activity.

Respiratory metadata describing the respiratory movements of the person is generated (step 1206). The respiratory metadata is analyzed to identify patterns of respiration (step 1208). A determination is made as to whether the patterns of respiration indicate behavioral deviations (step 1210). If the respiratory patterns do not indicate behavioral deviations, the process terminates thereafter. Returning to step 1210, if the patterns of respiration indicate behavior deviations, the person is identified as a person of interest (step 1212) with the process terminating thereafter.

Thus, the illustrative embodiments provide a computer implemented method, apparatus, and computer usable program code for detecting behavioral deviations in members of a cohort group. In one embodiment, a member of a cohort group is identified. Each member of the cohort group shares a common characteristic. Respiratory metadata associated with the member of the cohort group is received in real-time as the respiratory metadata is generated. The respiratory metadata describes respiration associated with the member of the cohort group. Patterns of respiratory changes are identified using the respiratory metadata. The respiratory metadata is analyzed to identify the patterns of respiratory changes. In response to the patterns of respiratory changes indicating behavioral deviations in the member of the cohort group, the member of the cohort group is identified as a person of interest.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention can take the form of an entirely software embodiment or an embodiment containing both hardware and software elements. In a preferred embodiment, the invention is implemented in software, which includes but is not limited to firmware, resident software, microcode, etc.

Furthermore, the invention can take the form of a computer program product accessible from a computer-usable or computer-readable medium providing program code for use by or in connection with a computer or any instruction execution system. For the purposes of this description, a computer-usable or computer readable medium can be any tangible apparatus that can contain, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

The description of the present invention has been presented for purposes of illustration and description, and is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated.

What is claimed is:

1. A computer implemented method for detecting behavioral deviations in members of a cohort group, the computer implemented method comprising:

identifying a member of the cohort group, wherein each member of the cohort group shares a common characteristic, and wherein the member is described using identification data, and further wherein the identification data includes: action data regarding the member's use of a web page, and device data regarding a computing device having a user interface and used by the member to interact with a data processing system associated with a transportation facility;

retrieving respiratory metadata in real-time as the respiratory metadata is generated, wherein the respiratory metadata is associated with the member of the cohort group, wherein the respiratory metadata describes respiration associated with the member of the cohort group;

identify patterns of respiratory changes using the respiratory metadata, wherein the respiratory metadata is analyzed to identify the patterns of respiratory changes;

responsive to the patterns of respiratory changes indicating behavioral deviations in the member of the cohort group, identifying the member of the cohort group as a person of interest;

analyzing audio data to identify human voices and phonetics of human speech to identify a voice print of the member of the cohort group, wherein the audio data describes non-respiratory characteristics of the member of the cohort group;

comparing the voice print of the member of the cohort group to each voice print included in a group of known voice prints to locate one of the voice prints included in the group of known voice prints that matches the voice print of the member of the cohort group; and using the one of the voice prints included in the group of known voice prints that matches the voice print of the member of the cohort group to identify the member of the coherent group, wherein the action data includes page hits, sequence of hits, duration of page views, response to advertisements, and transactions made.

2. The computer implemented method of claim 1 wherein the respiratory metadata comprises metadata-describing breath sounds and sounds associated with inspiration and expiration of air by a respiratory system of the member of the cohort group.

3. The computer implemented method of claim 1 further comprising:

analyzing event metadata associated with a plurality of individuals in real-time to identify individuals in the plurality of individuals that share the common characteristic, wherein the metadata describes events associated with each individual and patterns of behavior associated with the each individual; and identifying the individuals in the plurality of individuals that share the common characteristic to form the cohort group.

4. The computer implemented method of claim 3 wherein the transportation facility is an airport.

5. The computer implemented method of claim 1 wherein the cohort group is a group of people in a transportation facility.

6. The computer implemented method of claim 1 further comprising:

analyzing the patterns of respiration to identify a rate of respiration associated with the member of the cohort group.

7. The computer implemented method of claim 1 wherein the respiratory metadata comprises metadata describing changes in movements of a rib cage and abdomen of the member of the cohort group and further comprising:

analyzing the respiratory metadata to determine characteristics of the respiration by the member of the cohort group by determining if the member of the cohort group is exhibiting deep breathing, shallow breathing, fast breathing, and erratic breathing.

8. The computer implemented method of claim 1 wherein identifying patterns of respiratory changes using the respiratory metadata includes determining if the member of the cohort group is reacting in an atypical manner to external stimuli, the person is failing to display expected responses to external stimuli, the member of the cohort group is demonstrating an atypically high level of tension, the person is controlling their breathing, and the member of the cohort group is demonstrating a lack of emotion.

9. The computer implemented method of claim 1 further comprising:

responsive to identifying the member of the cohort group as the person of interest, increasing a level of monitoring associated with the person of interest.

10. A computer program product stored on a non-transistor computer-readable medium for detecting behavioral deviations in members of a cohort group, the computer program product comprising:

program code stored on the computer readable medium for identifying a member of the cohort group, wherein each member of the cohort group shares a common characteristic, and wherein the member is described using identification data, and further wherein the identification data includes: action data regarding the member's use of a web page, and device data regarding a computing device having a user interface and used by the member to interact with a data processing system associated with a transportation facility;

program code stored on the computer readable medium for retrieving respiratory metadata associated with the member of the cohort group in real-time as the respiratory metadata is generated, wherein the respiratory metadata describes respiration associated with the member of the cohort group;

program code stored on the computer readable medium for identifying patterns of respiratory changes using the respiratory metadata, wherein the respiratory metadata is analyzed to identify the patterns of respiratory changes;

program code stored on the computer readable medium for identifying the member of the cohort group as a person of interest in response to the patterns of respiratory changes indicating behavioral deviations in the member of the cohort group;

program code stored on the computer readable medium for analyzing audio data to identify human voices and phonetics of human speech to identify a voice print of the member of the cohort group, wherein the audio data describes non-respiratory characteristics of the member of the cohort group;
program code stored on the computer readable medium for comparing the voice print of the member of the cohort group to each voice print included in a group of known voice prints to locate one of the voice prints included in the group of known voice prints that matches the voice print of the member of the cohort group; and
program code stored on the computer readable medium for using the one of the voice prints included in the group of known voice prints that matches the voice print of the member of the cohort group to identify the member of the coherent group, wherein the action data includes page hits, sequence of hits, duration of page views, response to advertisements, and transactions made.

11. The computer program product of claim 10 wherein the respiratory metadata comprises metadata describing changes in movements of a rib cage and abdomen of the member of the cohort group and further comprising:
analyzing the respiratory metadata to determine characteristics of the respiration by the member of the cohort group by determining if the member of the cohort group is exhibiting deep breathing, shallow breathing, fast breathing, and erratic breathing.

12. An apparatus for detecting behavioral deviations in members of a cohort group, the apparatus comprising:
an analysis server, wherein the analysis server identifies a member of the cohort group based on data associated with the member of the cohort group gathered in real time, and wherein each member of the cohort group shares a common characteristic, and wherein the member is described using identification data, and further wherein the identification data includes: action data regarding the member's use of a web page, and device data regarding a computing device having a user interface and used by the member to interact with a data processing system associated with a transportation facility;
a video analysis system, wherein the video analysis system generates respiratory metadata associated with the member of the cohort group in real-time, wherein the respiratory metadata describes respiration by the member of the cohort group;
a respiratory pattern recognition engine, wherein the respiratory pattern recognition engine identifies patterns of respiratory changes associated with the respiration by the member of the cohort group using the respiratory metadata, wherein the respiratory metadata is analyzed to identify the patterns of respiratory changes;
a person of interest identification engine, wherein the person of interest identification engine identifies the member of the cohort group as a person of interest in response to the patterns of respiratory changes indicating behavioral deviations by the member of the cohort group;
a computer analyzing audio data to identify human voices and phonetics of human speech to identify a voice print of the member of the cohort group, wherein the audio data describes non-respiratory characteristics of the member of the cohort group;
the computer comparing the voice print of the member of the cohort group to each voice print included in a group of known voice prints to locate one of the voice prints included in the group of known voice prints that matches the voice print of the member of the cohort group; and
the computer using the one of the voice prints included in the group of known voice prints that matches the voice print of the member of the cohort group to identify the member of the coherent group, wherein the action data includes page hits, sequence of hits, duration of page views, response to advertisements, and transactions made.

13. The apparatus of claim 12 further comprising:
a cohort analysis component, wherein the cohort analysis component analyzes event metadata associated with a plurality of individuals to identify individuals in the plurality of individuals that share a common characteristic, wherein the metadata describes events associated with each individual and patterns of behavior associated with the each individual; and wherein the cohort analysis component identifies the individuals in the plurality of individuals that share the common characteristic to form the cohort group.

14. The apparatus of claim 12 further comprising:
a risk assessment engine, wherein the risk assessment engine identifies a level of risk associated with the person of interest; and wherein the risk assessment engine increases a level of monitoring associated with the person of interest in response to the level of risk associated with the person of interest exceeding a threshold level of risk.

15. The apparatus of claim 12 wherein the respiratory pattern recognition engine analyzes the patterns of respiration to identify a rate of respiration associated with the member of the cohort group.

* * * * *